United States Patent
Hirotsu et al.

(10) Patent No.: US 11,479,800 B2
(45) Date of Patent: Oct. 25, 2022

(54) CANCER DETECTION METHOD USING TISSUE SPECIMEN

(71) Applicants: HIROTSU BIO SCIENCE INC., Chiyoda-ku (JP); NANPUH HOSPITAL, Kagoshima (JP)

(72) Inventors: Takaaki Hirotsu, Tokyo (JP); Takuma Yoshinaga, Kagoshima (JP)

(73) Assignees: HIROTSU BIO SCIENCE INC., Chiyoda-ku (JP); NANPUH HOSPITAL, Kagoshima (JP)

( * ) Notice: Subject to any disclaimer, the term of this patent is extended or adjusted under 35 U.S.C. 154(b) by 288 days.

(21) Appl. No.: 16/630,277

(22) PCT Filed: Jul. 10, 2018

(86) PCT No.: PCT/JP2018/025975
§ 371 (c)(1),
(2) Date: Jan. 10, 2020

(87) PCT Pub. No.: WO2019/013187
PCT Pub. Date: Jan. 17, 2019

(65) Prior Publication Data
US 2020/0165655 A1    May 28, 2020

(30) Foreign Application Priority Data
Jul. 11, 2017  (JP) ............... JP2017-135174

(51) Int. Cl.
*C12Q 1/02* (2006.01)
*G01N 33/483* (2006.01)

(52) U.S. Cl.
CPC ........... *C12Q 1/02* (2013.01); *G01N 33/4833* (2013.01)

(58) Field of Classification Search
CPC ............ G01N 33/487; G01N 33/4833; G01N 33/5308; G01N 33/574–57496
See application file for complete search history.

(56) References Cited

U.S. PATENT DOCUMENTS

| | | | | |
|---|---|---|---|---|
| 11,150,234 B2 * | 10/2021 | Hirotsu | ............... | G01N 33/48 |
| 2017/0016906 A1 | 1/2017 | Hirotsu et al. | | |
| 2019/0369084 A1 | 12/2019 | Hirotsu et al. | | |

FOREIGN PATENT DOCUMENTS

| | | | | |
|---|---|---|---|---|
| CN | 106153879 A | 11/2016 | | |
| CN | 106255877 A | 12/2016 | | |
| CN | 106290169 A | 1/2017 | | |
| EP | 3081935 A1 * | 10/2016 | ........... | C12Q 1/6888 |
| JP | 2014-36656 A | 2/2014 | | |
| JP | 20160095135 * | 8/2016 | ....... | G01N 33/57488 |
| WO | WO 2015/088039 A1 | 6/2015 | | |
| WO | WO 2016/147268 A1 | 9/2016 | | |
| WO | WO 2018/047959 A1 | 3/2018 | | |

OTHER PUBLICATIONS

Biology Online Dictionary "Taxis" 3 pgs. 2019-2022 (Year: 2019).*
Moens et al. "Selective attraction of marine bacterivorous nematodes to their bacterial food" Marine Ecology Progress Series vol. 176: 165-178, 1999 (Year: 1999).*
International Search Report dated Oct. 9, 2018 in PCT/JP2018/025975 filed on Jul. 10, 2018, 2 pages.
Hirotsu et al., "A Highly Accurate Inclusive Cancer Screening Test Using Caenorhabditis elegans Scent Detection," PLOS One, Mar. 11, 2015, vol. 10, No. 3, pp. 1-15, DOI: 10.1371/journal.pone 0118699.
Combined Chinese Office Action and Search Report dated Jun. 23, 2020 in corresponding Chinese Patent Application No. 201880042246.1 (with English Translation of Category of Cited Documents), 6 pages.

* cited by examiner

*Primary Examiner* — Thane Underdahl
(74) *Attorney, Agent, or Firm* — Oblon, McClelland, Maier & Neustadt, L.L.P.

(57) ABSTRACT

The present invention provides a method for detecting cancer using a tissue specimen. Specifically, for example, there is provided a method for detecting cancer in an organ or tissue having cancer, comprising: preparing a cell lysate from a region suspected to be cancer isolated from the organ or tissue; and evaluating a tactic behavior of a nematode for the cell lysate.

6 Claims, 2 Drawing Sheets

CANCER DETECTION METHOD USING TISSUE SPECIMEN

TECHNICAL FIELD

The present invention provides a method for detecting cancer using a tissue specimen.

BACKGROUND ART

The nematode has been found to exhibit an attraction behavior to urine samples of cancer patients and to exhibit an avoidance behavior to urine samples of healthy subjects. A method for diagnosing cancer based on the tactic behavior of the nematode has been developed (Patent Literature 1). This evaluation system involves diluting a urine sample approximately 10 times and the subject which the sample is derived from can be evaluated as having cancer if the nematode exhibits an attraction behavior to the diluted sample. With a high dilution ratio, the precision of the evaluation largely decreases as matter of course (Patent Literature 1).

CITATION LIST

Patent Literature

Patent Literature 1: WO2015/088039

SUMMARY OF INVENTION

The present inventors considered that the technological development that makes it possible to distinguish between cancer tissue and normal tissue (for example, between cancer and normal tissue around the cancer) was necessary. The present invention provides a method for detecting cancer using a tissue specimen.

The present inventors examined, using a tissue specimen of cancer, the tactic behavior of the nematodes using cell lysates from the cancer and normal tissue around the cancer as test samples. As a result, the nematode was found to exhibit the attraction behavior to the cell lysate from the cancer tissue and to exhibit the avoidance behavior to the cell lysate from the normal tissue around the cancer.

The present invention is based on such findings.

Accordingly, the present invention provides, for example, the following inventions.

[1] A method for detecting cancer in a tissue specimen, comprising:
preparing a cell lysate from the tissue specimen or a cell lysate from a region suspected to be cancer isolated from the tissue specimen; and
evaluating a tactic behavior of a nematode for the cell lysate.

[2] A method for detecting a part not being cancer (non-cancerous part) in a tissue specimen, comprising:
preparing a cell lysate from the tissue specimen or a cell lysate from a region expected not to be cancer isolated from the tissue specimen; and
evaluating a tactic behavior of a nematode for the cell lysate.

[3] A method for distinguishing between a region being cancer and a region not being cancer in a tissue specimen, comprising:
preparing a cell lysate from a region suspected to be cancer isolated from the tissue specimen and a cell lysate from a region expected not to be cancer isolated from the tissue specimen; and
evaluating a tactic behavior of a nematode for each of the cell lysates.

[4] A method for distinguishing between a cell lysate derived from a tissue specimen comprising a cancer cell and a cell lysate derived from a tissue specimen comprising no cancer cell, comprising:
preparing cell lysates from a tissue specimen; and
evaluating a tactic behavior of a nematode for each of the cell lysates.

[5] A method for determining that a tissue specimen comprises no cancer, comprising:
preparing cell lysates from the tissue specimen; and
evaluating a tactic behavior of a nematode for each of the cell lysates.

[6] The method according to any of [1] to [5] above, wherein the evaluating of a tactic behavior of a nematode for the cell lysate involves mixing a solvent with a tissue section in a ratio of 1 to 10 mL of the solvent to 10 µm of the tissue section to obtain a cell lysate; and
diluting the cell lysate in dilution ratios ranging from $10^5$ to $10^7$ and evaluating a tactic behavior of a nematode for each of the resulting dilutions.

DESCRIPTION OF EMBODIMENTS

Figure 1:
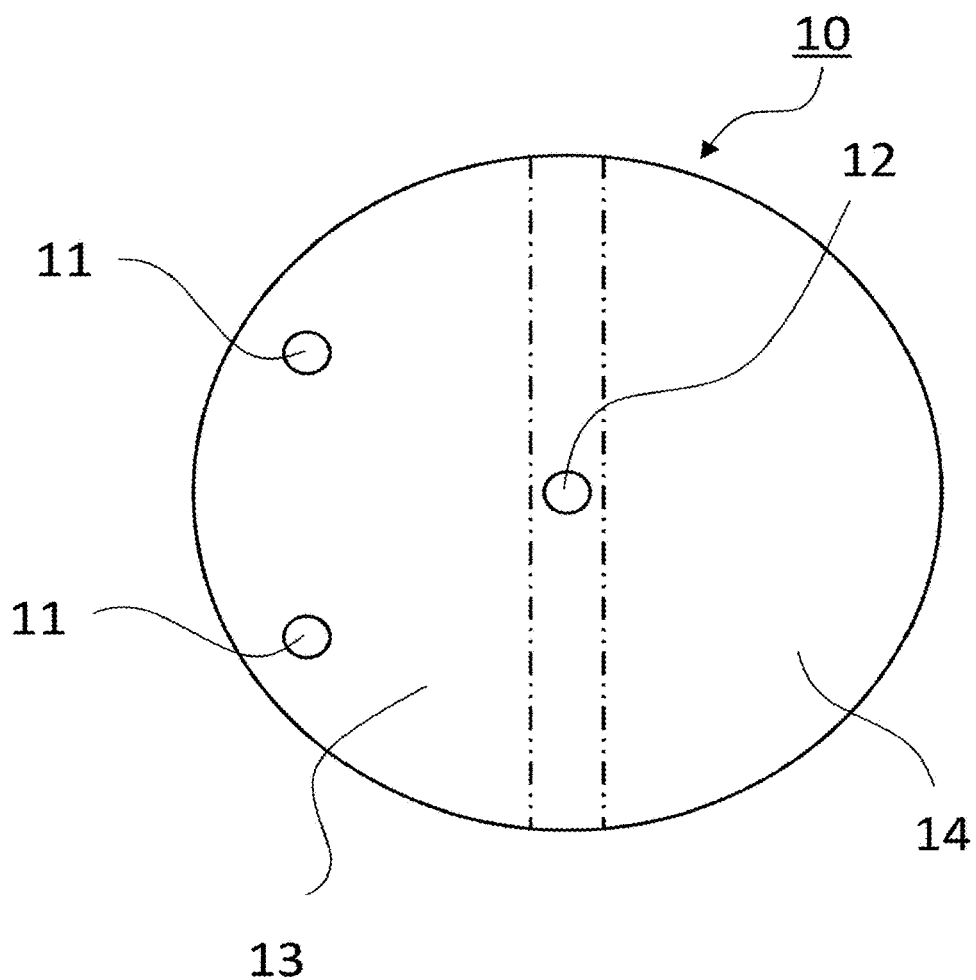
FIG. 1 illustrates a schematic diagram of an evaluation system for an attraction behavior using the nematode performed in Example 1. In this evaluation system, the tactic behavior of the nematode to a urine sample was evaluated on a laboratory dish containing an agar medium.

As used herein, the "nematode" means *Caenorhabditis elegans*. The nematode is a popular organism that is bred and studied as a model organism in biological studies widely all over the world and characterized by being easy to be bred and having a keen sense of smell.

As used herein, the "cancer" means such types of cancer as renal cancer, gastric cancer, uterine cancer, liver cancer, breast cancer, colorectal cancer, esophageal cancer, pancreatic cancer, prostate cancer, bile duct cancer, lung cancer, blood cancer, leukemia, and lymphoma.

As used herein, the "subject" means a mammal, for example, a human. The subject may be a subject having cancer or a subject suspected to have cancer (which may be hereinafter simply referred to as the "subject suspected of cancer").

In the present invention, the "tissue specimen" means all or a part of an organ or tissue derived from a subject, particularly a part of an organ or tissue derived from a subject. Examples of the tissue specimen include a specimen obtained by a biopsy (for example, a biopsy obtained in endoscopy) and a specimen that can be obtained at the time of an operation (for example, an organ or tissue removed by an operation). The tissue specimen may be an isolated cell or cell agglomerate. The "tissue specimen" may be all or a part of an organ or tissue suspected of cancer in many cases. As used herein, the "tissue specimen" may comprise a single part or a plurality of parts isolated from a single organ or tissue or may comprise a single part or a plurality of parts derived from each of a plurality of organs or tissues (in the same patient or different patients).

As used herein, the term "about" means including numerical values between the following numerical value plus and minus 10% or 5%.

As used herein, the term "tactic behavior" means an attraction behavior or an avoidance behavior. The attraction behavior means a movement to close the physical distance to a substance and the avoidance behavior means a movement to increase the physical distance from a substance. A substance that induces the attraction behavior is referred to as an attractant and a substance that induces the avoidance behavior is referred to as a repellent.

The nematode (*C. elegans*) has the properties of being attracted to attractants and avoiding repellents by sense of smell. An attraction to an attractant is referred to as an attraction behavior and an avoidance from a repellent is referred to as an avoidance behavior. The attraction behavior and the avoidance behavior are collectively referred to as tactic behaviors. The nematode exhibits an attraction behavior to urine samples of cancer patients and on the other hand, the nematode exhibits an avoidance behavior to urine samples of healthy subjects.

As used herein, "a method for detecting cancer" or a similar expression may also read as "a method for evaluating a tactic behavior of a nematode for detecting cancer", "a method for obtaining preliminary information about the presence or absence of cancer", "a method for obtaining preliminary information for a diagnosis of cancer", "a preliminary method for a diagnosis of cancer", or "a method for detecting a cancer cell". The information obtained in the present invention may be a base of a diagnosis by a medical practitioner as intermediate information.

[1] According to the present invention, a method for detecting cancer in a tissue specimen (or a method for obtaining preliminary information about the presence or absence of cancer, a method for obtaining preliminary information for a diagnosis of cancer, a preliminary method for the diagnosis of cancer, a method for detecting a cancer cell, or a method for a diagnosis of cancer), comprising:
(1) preparing a cell lysate from the tissue specimen or a cell lysate from a region suspected to be cancer isolated from the tissue specimen; and
(2) evaluating a tactic behavior of a nematode to the cell lysate.

In the present invention, the tissue specimen may be all or a part of an organ or tissue derived from a subject. In a certain aspect of the present invention, the subject may be a human subject. In a certain aspect of the present invention, the subject may be, for example, a subject suspected of cancer. In a certain aspect of the present invention, the subject may be, for example, a subject having cancer. In a certain aspect of the present invention, the subject may be a subject in need of an examination about the presence or absence of cancer. In a particular aspect of the invention, the subject may be a subject being operated, in particular a subject being operated for the removal of cancer.

(1) Preparing a Cell Lysate from the Tissue Specimen or a Cell Lysate from a Region Suspected to be Cancer Isolated from the Tissue Specimen In the above (1), the region suspected to be cancer may be isolated from a tissue specimen removed from the subject. In a certain aspect, the region suspected to be cancer may be isolated from a tissue specimen suspected to have cancer removed from the subject or from a tissue specimen having cancer removed from the subject. An amount of the tissue specimen equal to approximately several millimeters×several to several tens of millimeters×10 μm in thickness is sufficient for an evaluation. For example, if the thickness is 10 μm, then the area of the section may be 1 $mm^2$ or more, 2 $mm^2$ or more, 3 $mm^2$ or more, 4 $mm^2$ or more, 5 $mm^2$ or more, 6 $mm^2$ or more, 7 $mm^2$ or more, 8 $mm^2$ or more, 9 $mm^2$ or more, 10 $mm^2$ or more, 15 $mm^2$ or more, 20 $mm^2$ or more, 30 $mm^2$ or more, 40 $mm^2$ or more, or 50 $mm^2$ or more and may be 1,000 $mm^2$ or less, 900 $mm^2$ or less, 800 $mm^2$ or less, 700 $mm^2$ or less, 600 $mm^2$ or less, 500 $mm^2$ or less, 400 $mm^2$ or less, 300 $mm^2$ or less, 200 $mm^2$ or less, or 100 $mm^2$ or less.

In the above (1), the cell lysate may be obtained by various methods well-known to those skilled in the art. According to Patent Literature 1 (WO2015/088039) mentioned above, the nematode exhibited an attraction behavior to urine samples from cancer patients and exhibited an avoidance behavior to urine samples from healthy subjects. From this, it was expected that urine contains a cancer-specific secretory factor secreted from cancer tissue or cancer cells. Taking into account that the nematode exhibits the tactic behavior to a cancer-specific secretory factor, it was considered that the secretory factor may also contained in normal tissue in proximity to the cancer tissue or cancer cells and thereby the nematode may exhibit an attraction behavior to the normal tissue in proximity to the cancer tissue or cancer cells. However, according to Examples described below, a region being cancer and a normal region (non-cancerous region) adjacent thereto in the same specimen induced the nematode to exhibit different tactic behaviors. More specifically, the nematode exhibits an attraction behavior to the region being cancer and the nematode exhibits an avoidance behavior to the normal region adjacent thereto. This is considered to indicate that an intracellular factor in cancer cells has a stronger effect on the tactic behavior of the nematode than secretory factors from cancer. Moreover, the intracellular factor in cancer cells that was detected by the sense of smell of the nematode was a factor that can be detected at high dilution ratios.

Accordingly, the cell lysate, in the present invention, may be obtained by any method, as long as the method allows the use of a cell lysate from tissue and disruption of cells to extract intracellular factors. The method for obtaining a cell lysate from tissue or cells is not particularly limited, but examples thereof include methods with an ultrasonic disruptor, methods involving application of pressure, methods by agitation, methods involving grind, and methods involving a water stream. The solvent for obtaining the cell lysate may be, for example, ethanol or water.

In a certain aspect of the present invention, a tissue section and a solvent can be mixed at a ratio of, for example, 1 to 10 mL, 2 to 8 mL, 3 to 7 mL, 4 to 6 mL, or about 5 mL of the solvent to the tissue section having a thickness of 10 μm from a specimen to obtain a cell lysate from this mixture.

In a certain aspect of the present invention, a tissue specimen known to be cancer or urine of a cancer patient can be used as a positive control. In a certain aspect of the present invention, a tissue specimen known to contain no cancer or a part thereof or urine of a subject known to have no cancer (for example, a healthy subject) can be used as a negative control.

The above (1) may comprise (1-A) preparing a region suspected to be cancer isolated from the organ or tissue; and (1-B) obtaining a cell lysate from the region.

(2) Evaluating a Tactic Behavior of a Nematode to the Cell Lysate

In the above (2), a dilution resulting from diluting a cell lysate with a solvent may be used as a cell lysate.

In the present invention, the dilution ratio in the dilution described above varies depending on the cancer specimen used, but it may be considered to dilute a cell lysate obtained from a section having a thickness of 10 μm by using, for example, 1 to 10 mL (for example, 2 to 8 mL, 3 to 7 mL, 4 to 6 mL, or about 5 mL) of a solvent with a solvent at a ratio of approximately 10,000-fold to 1,000,000-fold, approximately 20,000-fold to 500,000-fold, approximately 50,000-fold to 300,000-fold, or approximately about 100,000-fold to the cell lysate. A person skilled in the art would be able to adjust the dilution ratio as appropriate in light of the amount of the tissue specimen. Moreover, a dilution series (a dilution series that covers dilution ratios within the range of ratios described above; for example, a dilution series of 2-fold to 10-fold, for example, a dilution series of 3-fold to 5-fold, for example, a dilution series of 5-fold to 15-fold) of a cell lysate may be prepared for examination.

In the present invention, the dilution of the cell lysate may be prepared with a solvent, for example, ethanol, water, for example, distilled water or sterile water.

Whether a nematode exhibits an attraction behavior to a cell lysate or not can be evaluated by observing whether the nematode moves toward or away from the cell lysate disposed at a certain distance (for example, 1 to 5 cm) from the nematode. If some nematodes move toward the cell lysate and some nematodes move away from the cell lysate, it may be evaluated that the nematodes exhibit an attraction behavior to the cell lysate when the ratio of the nematodes that move toward the cell lysate is higher than the ratio of the nematodes that move away from the cell lysate. It may also be evaluated that the nematodes exhibit an avoidance behavior to the cell lysate when the ratio of the nematodes that move toward the cell lysate is lower than the ratio of the nematodes that move away from the cell lysate. Nematodes of any nematode strain may be used as long as they exhibit an attraction behavior to urine or tissue of cancer patients, and, for example, wildtype nematode strains, for example, the strain Briostol N2, particularly hermaphroditic individuals of the strain, may be used.

Moreover, whether nematodes exhibit an attraction behavior or an avoidance behavior may be evaluated, for example, by determining the tactic index from the following equation.

Tactic Index (Tactic index)={(the number of nematode individuals that move toward the cell lysate)–(the number of nematode individuals that move away from the cell lysate)}/the total number of nematode individuals The tactic index is a numerical value ranging from –1 to +1 and takes on a positive value when an attraction behavior is exhibited and a negative value when an avoidance behavior is exhibited. The larger numerical absolute value is construed as the exhibition of the stronger tactic behavior.

In a certain aspect, the method according to the present invention may further comprises:
(3) evaluating whether the cell lysate is an attractant or a repellent based on the tactic behavior that the nematode exhibits to the cell lysate.

In the method according to the present invention, if the nematode exhibits an attraction behavior to a cell lysate, then it is indicated that the tissue specimen or the region suspected to be cancer which the cell lysate is derived from has cancer or a possibility of having cancer. In the method according to the present invention, if the nematode, for example, exhibits an avoidance behavior to a cell lysate, then it is indicated that the tissue specimen or the region suspected to be cancer which the cell lysate is derived from has no cancer or a possibility of having no cancer. When a dilution series of a cell lysate is used, if the nematode exhibits an attraction behavior for any one or more in the dilution series, then it is indicated that the tissue specimen or the region suspected to be cancer which the cell lysate is derived from has cancer or a possibility of having cancer. Whether there is an attraction behavior or not may be evaluated based on whether the tactic index described above is above 0 or not as an indicator or based on whether a stronger attraction behavior in comparison with a negative control is exhibited as an indicator, or based on a combination thereof.

[2] The present invention provides a method for detecting a part not being cancer in a tissue specimen, comprising:
(1) preparing a cell lysate from the tissue specimen or a cell lysate from a region expected not to be cancer isolated from the tissue specimen; and
(2) evaluating a tactic behavior of a nematode to the cell lysate.

In the present invention, the tissue specimen may be all or a part of an organ or tissue derived from a subject. In a certain aspect of the present invention, the subject may be a human subject. In a certain aspect of the present invention, the subject may be, for example, a subject suspected of cancer. In a certain aspect of the present invention, the subject may be, for example, a subject having cancer. In a certain aspect of the present invention, the subject may be a subject in need of an examination about the presence or absence of cancer. In a particular aspect of the present invention, the subject may be a subject being operated, in particular a subject being operated for the removal of cancer.

In the above [2] (1), the region expected not to be cancer may be isolated from a tissue specimen removed from the subject. In a certain aspect, the region expected not to be cancer may be isolated from a tissue specimen suspected to have cancer (the tissue specimen includes a region suspected to have cancer and a region expected not to be cancer) removed from the subject or may be isolated from a tissue specimen having cancer, or may be isolated from a tissue specimen expected to have no cancer or may be isolated from a tissue specimen having no cancer.

In the above [2] (1), the cell lysate can be obtained by various methods well-known to those skilled in the art. The details are as described in detail for [1] (1).

The above [2] (1) may comprise (1-A) preparing a region expected not to be cancer isolated from the tissue specimen; and (1-B) obtaining a cell lysate from the region.
(2) Evaluating the Tactic Behavior of a Nematode to the Cell Lysate The above [2] (2) is as described in detail for the above [1] (2).

In a certain aspect, the method according to the present invention may further comprise:
(3) evaluating whether the cell lysate is an attractant or a repellent based on the tactic behavior that the nematode exhibits to the cell lysate.

In the method according to the present invention, if a nematode exhibits an attraction behavior to a cell lysate, then it is indicated that the tissue specimen or the region suspected to be cancer which the cell lysate is derived from has cancer or a possibility of having cancer. In the method according to the present invention, if a nematode exhibits, for example, an avoidance behavior to a cell lysate, then it is indicated that the tissue specimen or the region suspected to be cancer which the cell lysate is derived from has no cancer or a possibility of having no cancer.

[3] The present invention provides a method for distinguishing (identifying, differentiating, classifying, or diagnosing with cancer) between a region being cancer and a region not being cancer in a tissue specimen, comprising:

(1) preparing a cell lysate from a region suspected to be cancer isolated from the tissue specimen and a cell lysate from a region expected not to be cancer isolated from the tissue specimen; and (2) evaluating a tactic behavior of a nematode to each of the cell lysates.

In the present invention, the tissue specimen may be all or a part of an organ or tissue derived from a subject. In a certain aspect of the present invention, the subject may be a human subject. In a certain aspect of the present invention, the subject may be, for example, a subject suspected of cancer. In a certain aspect of the present invention, the subject may be, for example, a subject having cancer. In a certain aspect of the present invention, the subject may be a subject in need of an examination about the presence or absence of cancer. In a particular aspect of the present invention, the subject may be a subject being operated, in particular a subject being operated for the removal of cancer.

For the above [3] (1), the region suspected to be cancer is as described in detail for [1] (1) and the region expected not to be cancer is as described in detail for the above [2] (1).

The above [3] (2) is as described in detail for the above [1] (2).

In a certain aspect, the method according to the present invention may further comprise:

(3) evaluating whether the cell lysate is an attractant or a repellent based on the tactic behavior that the nematode exhibits to the cell lysate.

In the method according to the present invention, if the nematode exhibits an attraction behavior to a cell lysate, then it is indicated that the tissue specimen or the region suspected to be cancer which the cell lysate is derived from has cancer or a possibility of having cancer. In the method according to the present invention, if the nematode, for example, exhibits an avoidance behavior to a cell lysate, then it is indicated that the tissue specimen or the region suspected to be cancer which the cell lysate is derived from has no cancer or a possibility of having no cancer.

[4] The present invention provides a method for determining whether a cell lysate is derived from a tissue specimen including a cancer cell or from a tissue specimen including no cancer cell, comprising:

(1) preparing cell lysates from a tissue specimen; and
(2) evaluating a tactic behavior of a nematode to each of the cell lysates.

In the present invention, the tissue specimen may be all or a part of an organ or tissue derived from the subject and may be, for example, a tissue specimen derived from an organ or the tissue having no cancer; or a tissue specimen derived from an organ or tissue having cancer (for example, a marginal, a fringe, or the like of a cancer). In a certain aspect of the present invention, the subject may be a human subject. In a certain aspect of the present invention, the subject may be, for example, a subject suspected of cancer. In a certain aspect of the present invention, the subject may be, for example, a subject having cancer. In a certain aspect of the present invention, the subject may be a subject in need of an examination about the presence or absence of cancer. In a particular aspect of the invention, the subject may be a subject being operated, in particular a subject being operated for the removal of cancer.

The above [4] (1) may be obtained by a method as described in detail for [1] (1).

The above [4] (2) is as described in detail for the above [1] (2).

In a certain aspect, the method according to the present invention may further comprise:

(3) evaluating whether the cell lysate is an attractant or a repellent based on the tactic behavior that the nematode exhibits to the cell lysate.

In the method according to the present invention, if the nematode exhibits an attraction behavior to the cell lysate, then it is indicated that the tissue specimen which the cell lysate is derived from is a tissue specimen having cancer or having a possibility to comprise cancer. In the method according to the present invention, if the nematode exhibits, for example, an avoidance behavior to the cell lysate, then it is indicated that the tissue specimen which the cell lysate is derived from is a tissue specimen having no cancer or having a possibility to comprise no cancer.

In the above [4], the specimen may be divided into a plurality of parts and respective cell lysates may be obtained from the plurality of parts to evaluate the tactic behavior of the nematode to each of the cell lysates. In this case, if a nematode exhibits an attraction behavior to at least one of the divided parts, then it is indicated that the specimen which the cell lysates are derived from is a specimen having cancer or having a possibility to have cancer. If the nematode exhibits an avoidance behavior to the cell lysates from all of the parts, then it is indicated that the specimen which the cell lysates are derived from is a specimen having no cancer or having a possibility to have no cancer.

[5] The present invention provides a method for determining that a tissue specimen comprises no cancer, comprising:

(1) preparing cell lysates from the tissue specimen; and
(2) evaluating a tactic behavior of a nematode to each of the cell lysates.

In the present invention, the specimen may be an organ or tissue derived from the subject. In a certain aspect of the present invention, the subject may be a human subject. In a certain aspect of the present invention, the subject may be, for example, a subject suspected of cancer. In a certain aspect of the present invention, the subject may be, for example, a subject having cancer. In a certain aspect of the present invention, the subject may be a subject in need of an examination about the presence or absence of cancer. In a particular aspect of the invention, the subject may be a subject being operated, in particular a subject being operated for the removal of cancer.

For the above [5] (1), the specimen may be obtained from, for example, an organ or tissue comprising a region suspected to be cancer or a region expected not to be cancer. The region suspected to be cancer or region expected not to be cancer is as described in detail for the above [1] (1) and [2] (1).

The above [5] (2) is as described in detail for the above [1] (2).

In a certain aspect, the method according to the present invention may further comprise:

(3) evaluating whether the cell lysate is an attractant or a repellent based on the tactic behavior that the nematode exhibits to the cell lysate.

In the method according to the present invention, if the nematode exhibits an attraction behavior to the cell lysate, then it is indicated that the specimen which the cell lysate is derived from has cancer or has a possibility to have cancer. In the method according to the present invention, if the nematode exhibits, for example, an avoidance behavior to the cell lysate, then it is indicated that the specimen which the cell lysate is derived from has no cancer or has a possibility to have no cancer.

In the above [5], the specimen may be divided into a plurality of parts and cell lysates may be obtained from each of parts to evaluate the tactic behavior of the nematode to each of the cell lysates. In this case, if a nematode exhibits an attraction behavior to at least one of the divided parts, then it is indicated that the specimen which the cell lysates are derived from has cancer or has a possibility to have cancer. If the nematode exhibits an avoidance behavior to the cell lysates from all of the parts, then it is indicated that the specimen which the cell lysates are derived from has no cancer or has a possibility to have no cancer.

The present invention provides a kit for diagnosing cancer tissue with cancer, comprising:
a nematode, a cell lysis buffer solution, and a diluent.
The subject, the dilution solvent, the dilution ratio, the method for evaluating the tactic behavior, the method for detecting cancer are as described above.

The present invention provides a kit for diagnosing cancer comprising a nematode, which kit is use for cancer tissue, the kit comprising the nematode, a cell lysis buffer solution, and a diluent; and being to be used in the method according to the present invention. The subject, the dilution solvent, the dilution ratio, the method for evaluating the tactic behavior, the method for detecting cancer are as described above.

As used herein, the "method for detecting cancer" or the "method for treating cancer" may further comprise, in addition to the aforementioned method for detecting cancer, treating the cancer with an appropriate cancer therapy. Accordingly, the present invention provides a method for treating cancer, comprising detecting cancer by a method for detection according to the present invention; and treating cancer in a subject in which cancer is detected. The cancer may be treated by a cancer therapy suitable for the cancer (for example, the administration of an anticancer agent, radiotherapy, immunotherapy for the cancer).

In particular, the method according to the present invention using a nematode may be performed by obtaining a cell lysate from surface tissue in cancer tissue derived from a subject being operated for the removal of cancer. If it is indicated, as a result, that there is cancer in the surface or there is a possibility thereof, then it can be judged that cancer may be left in a patient's organ or tissue that has been in contact with the surface. If it is judged that cancer may be left in the patient's organ or tissue that has been in contact with the surface, then the patient's organ or tissue that has been in contact with the surface may be removed more extensively. If the method according to the present invention is further performed also after the more extensive removal and cancer is still detected in the surface of tissue additionally removed, then the patient's organ or tissue that has been in contact with the surface may be removed even more extensively. In this way, the present invention can provide basic information for conducting an examination during an operation and judging, based on the result, whether tissue should be removed more extensively or not.

In a certain aspect of the present invention, a method for evaluating a tactic behavior of a nematode to a specimen sample, comprising:
preparing a cell lysate from the tissue specimen or a cell lysate from a region suspected to be cancer isolated from the tissue specimen; and
evaluating a tactic behavior of a nematode for the cell lysate, is provided. The cell lysate may be diluted or in a dilution series and the tactic behavior of the nematode may be evaluated with the tactic index.

The present invention is described referring to Examples, below. Examples are for the illustration purpose and should not be construed as limiting the scope of the invention.

EXAMPLES

Example 1: Examination for Cancer Using Nematode and Tissue Specimen of Cancer as Test Sample It is often difficult to distinguish between cancer tissue and non-cancer tissue in the same organ. In this Example, it was tested whether the nematodes can distinguish between cancer tissue and non-cancer tissue in the same organ.

Figure 2:
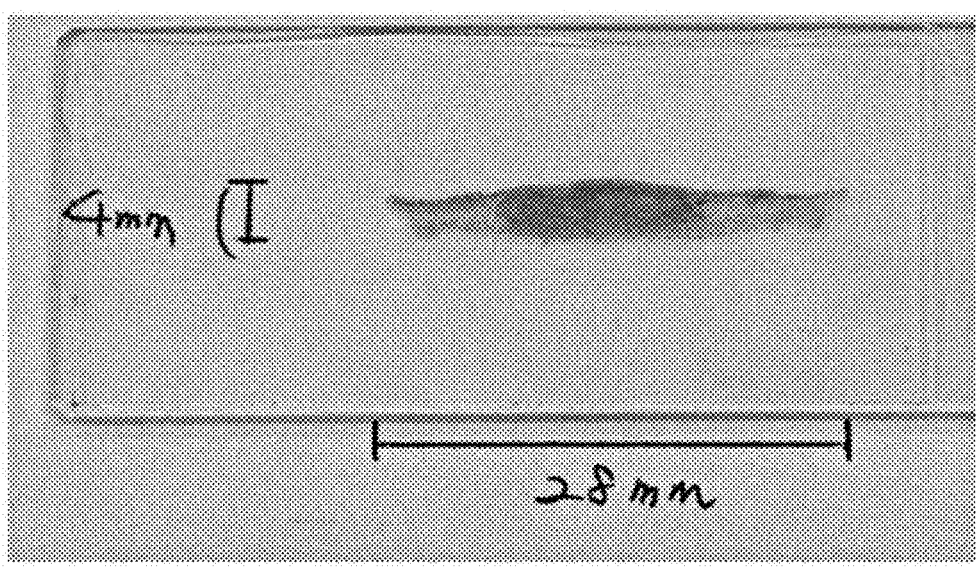
FIG. 2 shows a section of a tumor specimen used in Example 1.

First, a cancer tissue (the cancer tissue had normal tissue around the cancer tissue) removed from a gastric cancer patient was embedded in paraffin by a routine method after the formalin fixation and tissue sections having a thickness of 10 μm were prepared (see FIG. 2). The tissue section used was 4 mm×28 mm×10 μm in thickness. A cancerous part and a non-cancerous part were identified by a pathologist and 3 sections of each part were placed in 50 mL centrifuge tubes, respectively. 5 mL of 99% ethanol was added. Homogenates (cell lysates) of the cancerous parts and homogenates of the non-cancerous parts were obtained with an ultrasonic homogenizer (Sonifier 250A). 3 cases of each cancerous part and 3 cases of each non-cancerous part were collected and respective homogenates were obtained. Each homogenate was diluted 10-fold to $10^6$-fold with sterile water. A urine sample (100-fold dilution) of a cancer patient was used as a positive control and a urine sample (100-fold dilution) of a healthy subject was used as a negative control.

As shown in FIG. 1, a urine sample was diluted 100-fold with sterile water and applied at marginals 11 on the surface of a flat agar plate 10 and nematodes were applied in the central part 12 on the aforementioned agar plate and then it was observed whether the nematodes exhibit an attraction behavior or an avoidance behavior to the urine sample. Whether the nematodes exhibited an attraction behavior or an avoidance behavior was evaluated with the following tactic index. The nematodes used were hermaphroditic individuals of the strain Briostol N2.

Tactic Index (Tactic index)={(the number of nematode individuals in region 13)−(the number of nematode individuals in region 14)}/the total number of nematode individuals wherein the region 13 is the region on the urine sample side when the agar plate 10 is divided into 3 regions with long dashed double-dotted lines; and the region 14 is the region apart from the urine sample among the aforementioned 3 regions.

Figure 3:
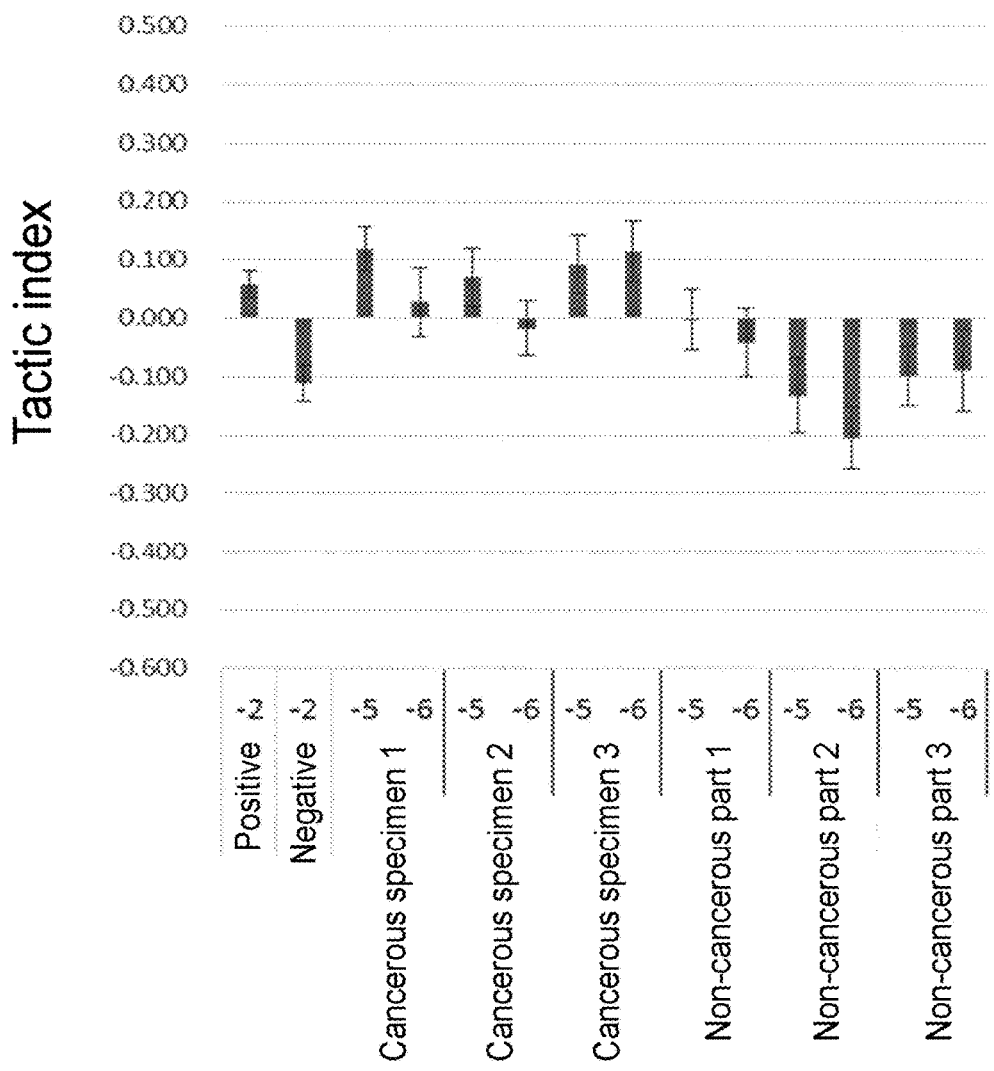
FIG. 3 shows the results of evaluation of the attraction behavior to cell lysates from cancer tissues using the nematode.

The results were as illustrated in FIG. 3. In FIG. 3, the $10^n$-fold dilution is indicated with "−n".

As shown in FIG. 3, the nematodes exhibited an attraction behavior to the samples with $10^5$-fold or $10^6$-fold dilution of the cell lysates from tissue in the cancerous parts, while the nematodes exhibited an avoidance behavior to the cell lysates from tissue in the non-cancerous parts, in contrast. The tactic behavior of the nematodes was not stable to the cell lysates with $10^1$-fold to $10^4$-fold dilution. It was found that dilution of cell lysates is desirable.

As seen above, the nematodes exhibited not only an attraction behavior to cell lysates from tissue in cancerous parts, but also an avoidance behavior to cell lysates from tissue in non-cancerous parts in the same tissue and was able to distinguish between the cancerous part and the non-cancerous part.

The invention claimed is:

1. A method for detecting cancer in a tissue specimen, comprising:
   preparing a cell lysate from the tissue specimen or a cell lysate from a region suspected to be cancer isolated from the tissue specimen;
   placing separately nematodes and the cell lysate on a plate to induce taxis behavior of the nematodes; and
   evaluating a taxis behavior of a nematode for the cell lysate,
   wherein an approaching behavior of the nematodes indicates that the tissue specimen contains cancer.

2. A method for detecting a non-cancerous part in a tissue specimen, comprising:
   preparing a cell lysate from the tissue specimen or a cell lysate from a region expected not to be cancer isolated from the tissue specimen;
   placing separately nematodes and the cell lysate on a plate to induce taxis behavior of the nematodes; and
   evaluating a taxis behavior of a nematode for the cell lysate,
   wherein an avoidance behavior of the nematodes indicates the noncancerous part in the tissue specimen.

3. A method for distinguishing between a region containing cancer and a region not containing cancer in a tissue specimen, comprising:
   preparing a cell lysate from a region suspected to be cancer isolated from the tissue specimen and a cell lysate from a region expected not to be cancer isolated from the tissue specimen;
   placing separately nematodes and the cell lysate on a plate to induce taxis behavior of the nematodes; and
   evaluating a taxis behavior of a nematode for each of the cell lysates,
   wherein an approaching behavior of the nematodes indicates the region contains cancer and wherein an avoidance behavior of the nematodes indicates that the region does not contain cancer.

4. The method according to claim 1, wherein the evaluating of a taxis behavior of a nematode for the cell lysate comprises mixing a solvent with a tissue section in a ratio of 1 to 10 mL of the solvent to 10 μm thickness of the tissue section having an area between 1 $mm^2$ or more and 1,000 $mm^2$ or less to obtain a cell lysate; and diluting the cell lysate in dilution ratios ranging from $10^5$ to $10^7$ and evaluating a taxis behavior of a nematode for each of the resulting dilutions.

5. The method according to claim 2, wherein the evaluating of a taxis behavior of a nematode for the cell lysate comprises mixing a solvent with a tissue section in a ratio of 1 to 10 mL of the solvent to 10 μm thickness of the tissue section having an area between 1 $mm^2$ or more and 1,000 $mm^2$ or less to obtain a cell lysate; and diluting the cell lysate in dilution ratios ranging from $10^5$ to $10^7$ and evaluating a taxis behavior of a nematode for each of the resulting dilutions.

6. The method according to claim 3, wherein the evaluating of a taxis behavior of a nematode for the cell lysate comprises mixing a solvent with a tissue section in a ratio of 1 to 10 mL of the solvent to 10 μm thickness of the tissue section having an area between 1 $mm^2$ or more and 1,000 $mm^2$ or less to obtain a cell lysate; and diluting the cell lysate in dilution ratios ranging from $10^5$ to $10^7$ and evaluating a taxis behavior of a nematode for each of the resulting dilutions.

* * * * *